(12) United States Patent
Hyde et al.

(10) Patent No.: US 6,908,208 B1
(45) Date of Patent: Jun. 21, 2005

(54) LIGHT TO BE WORN ON HEAD

(76) Inventors: Raymond Quentin Hyde, 36691 Sawmill La., Purcellville, VA (US) 20132-2617; Timothy Robert Cherry, R.R. 4, Box 319C, Loogootee, IN (US) 47553-9160

( * ) Notice: Subject to any disclaimer, the term of this patent is extended or adjusted under 35 U.S.C. 154(b) by 0 days.

(21) Appl. No.: 10/749,516

(22) Filed: Jan. 2, 2004

(51) Int. Cl.$^7$ ............................................. F21V 21/084
(52) U.S. Cl. ...................... 362/105; 362/108; 362/183; 362/294; 362/373; 362/804
(58) Field of Search ................................ 362/105, 106, 362/108, 183, 294, 373, 804

(56) References Cited

U.S. PATENT DOCUMENTS

| | | |
|---|---|---|
| 3,214,809 A | 11/1965 | Edwards |
| 4,613,931 A | 9/1986 | Messinger |
| 5,115,382 A | 5/1992 | Smith |
| 5,295,052 A | 3/1994 | Chin et al. |
| 5,457,611 A | 10/1995 | Verderber |
| 5,473,524 A | 12/1995 | Behringer |
| 6,039,461 A * | 3/2000 | Cummings et al. ......... 362/294 |
| D425,643 S | 5/2000 | Jigamian et al. |
| 6,340,237 B1 | 1/2002 | Koga et al. |
| 2002/0172033 A1 | 11/2002 | Bulko et al. |

FOREIGN PATENT DOCUMENTS

EP 0 933 067 8/1999

* cited by examiner

Primary Examiner—Stephen F Husar
(74) Attorney, Agent, or Firm—Stephen Christopher Swift; Swift Law Office

(57) ABSTRACT

A light that can be worn on the head of a user. Although designed originally to be a surgical headlight for use in equine dentistry, it may be used for any purpose in which a light mounted on the user's head is desirable, e.g., lighting a tunnel in a mine. In the preferred embodiment, a headband retains a halogen lamp on the user's head. The lamp is cooled by a combination of a fan similar to that used to cool personal computers, and fins that act as a heat sink to conduct heat away from the light to the surrounding air, where it is carried away by convection. The lamp and the fan can be turned on and off by a switch on the headband. They can be powered by a battery pack. The switch has a cylindrical button that slides back and forth between the on and off position.

20 Claims, 9 Drawing Sheets

LIGHT TO BE WORN ON HEAD

BACKGROUND OF THE INVENTION

1. Field of the Invention

The present invention relates to lights to be worn on the head of a user.

2. Description of the Prior Art

It is desirable for physicians, dentists, and veterinarians to have a light that can be worn on the doctor's head while they are examining a patient, which can be cooled to prevent it from overheating.

U.S. Pat. No. 3,214,809, issued on Nov. 2, 1965, to George Zahnor Edwards, discloses headgear having an adjustable headband, with an adjustable traverse strip that extends over the crown of the wearer's head. It does not disclose a light attached to the headband, as in the instant invention.

U.S. Pat. No. 4,613,931, issued on Sep. 23, 1986, to Elmar K. Messinger, discloses a portable fiber optic light source for use in hazardous locations, which uses cooling fins to carry heat away from the light. The instant invention is distinguishable, in that in it the halogen light is cooled by a fan as well as fins, and it has a headband by which the light may be worn on the head of its user.

U.S. Pat. No. 5,115,382, issued on May 19, 1992, to Robert C. Smith, discloses a headlamp apparatus, with a halogen lamp, an adjustable headband and rechargeable batteries. The instant invention is distinguishable, in that in it the lamp is cooled by a fan and fins.

U.S. Pat. No. 5,295,052, issued on Mar. 15, 1994, to Noelle C. Chin and Ernest E. Beland, Jr., discloses a light source assembly for medical and surgical applications, with a xenon lamp supported by heat sinks having the form of mounting plates with fins, and fans that provide an airflow. Light from the lamp is transmitted through fiber optic connections. The instant invention is distinguishable, in that it is designed to be worn on the head of the user, rather than contained within a stationary chassis, and light is provided directly from the lamp to the space to be illuminated, rather than through fiber optic connections.

U.S. Pat. No. 5,457,611, issued on Oct. 10, 1995, to Gregory R. Verderber, discloses an ambient air cooled light emitting instrument. A lamp is contained in a heat sink mounted in a housing having a plurality of vent holes. The instrument is designed to be held in the hand, rather than worn on the head. There is no fan, as in the instant invention.

U.S. Pat. No. 5,473,524, issued on Dec. 5, 1995, to Wolfgang Behringer, discloses a field of action light for medical and dental practice. It has a carrying strap that can be secured to a wall or ceiling bracket. It has lamp, which preferably is a halogen lamp, that is cooled by a "ventilator" or fan. Air is moved in one direction through a cylindrical housing, giving a "chimney effect". The instant invention is distinguishable, in that it is designed to be worn on the head, and it uses fins to cool the lamp, rather than a chimney effect.

U.S. Pat. No. 6,340,237, issued on Jan. 22, 2002, to Ritsuo Koga and Hideto Kubouchi, discloses a lamp cartridge, with a reflecting mirror and a fan in one side of the cartridge to cool the lamp. The components may be miniaturized. The instant invention is distinguishable, in that it is designed to be worn on the user's head.

U.S. Pat. No. Des. 425,643, issued on May 23, 2000, to Gregory Z. Jigamian, Jeffrey P. Kennedy and George Pelling, discloses a design for a portable focused beam searchlight, with a finned heat sink. No fan or strap is disclosed, as in the instant invention.

U.S. Patent Application Publication No. 2002/0172033, published on Nov. 21, 2002, inventors John M. Bulko, Gerald L. Yeaney and Michael A. Taft, discloses a surgical light apparatus with improved cooling. No fan is used, nor is it designed to be worn on the user's head, as in the instant invention.

European Patent Application No. 933 067, published on Aug. 4, 1999, inventors Bruno Senn, Gregor Fritsche and Gottfried Rohner, discloses a light curing apparatus, designed for curing dental materials in a patient's mouth, in which the lamp housing has cooling fins.

None of the above inventions and patents, taken either singly or in combination, is seen to describe the instant invention as claimed.

SUMMARY OF THE INVENTION

The present invention is a light that can be worn on the head of a user. Although designed originally to be a surgical headlight for use in equine dentistry, it may be used for any purpose in which a light mounted on the user's head is desirable, e.g., lighting a tunnel in a mine. In the preferred embodiment, a headband retains a halogen lamp on the user's head. The lamp is cooled by a combination of a fan similar to that used to cool -personal computers, and fins that act as a heat sink to conduct heat away from the light to the surrounding air, where it is carried away by convection. The lamp and the fan can be turned on and off by a switch on the headband. It can be powered by a battery pack or directly from a wall socket.

Accordingly, it is a principal object of the invention to provide a light that can be worn on the head by a veterinarian when performing equine dentistry, to illuminate the interior of a horse's mouth.

It is another object of the invention to provide a light that can be worn on the head of any health care professional, to illuminate any part of the body of a human or animal.

It is a further object of the invention to provide a light that can be worn on the head of any person, for any purpose for which a light mounted on the user's head is desirable.

Still another object of the invention is to provide a bright light that can be worn on the user's head without overheating.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 6 is a left side elevational view of the preferred embodiment of the invention, with the lamp in a raised position and the switch turned on.

Similar reference characters denote corresponding features consistently throughout the attached drawings.

DETAILED DESCRIPTION OF THE PREFERRED EMBODIMENT

The present invention is a light mounted to a headband that can be used as a surgical headlight or for other purposes.

Figure 1:
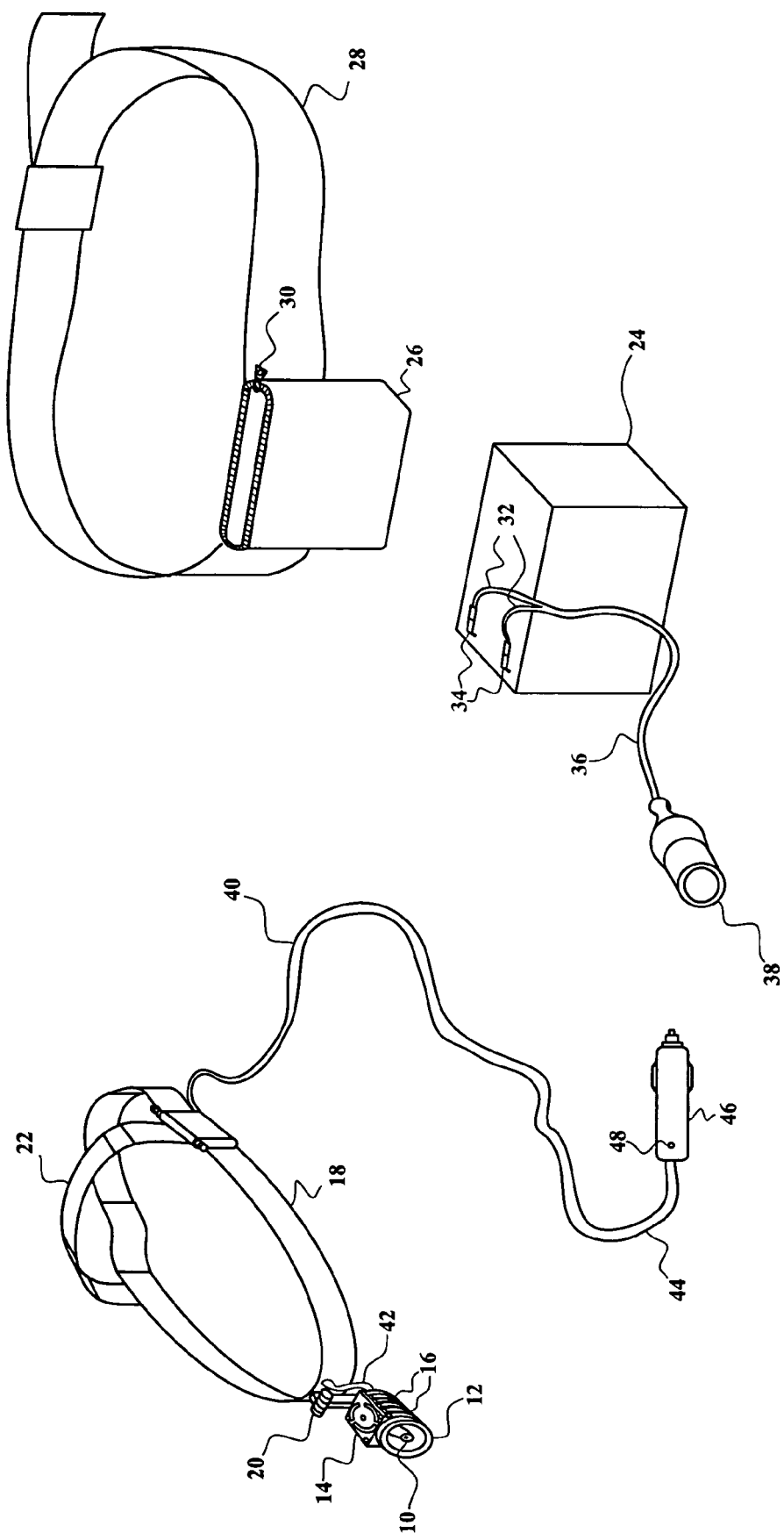
FIG. 1 is schematic perspective view of the preferred embodiment of the invention, with the power supply from the battery to the lamp and fan being disconnected, and the battery being shown outside its pouch.

FIG. 1 is schematic perspective view of the preferred embodiment of the invention, showing the halogen lamp 10 in its housing 12. (Alternatively, other kinds of electric lights may be used in place of the halogen lamp.) The lamp is cooled by the combination of a fan 14 mounted in a side wall of the housing (which is similar to the kinds of fans commonly used to cool personal computers) and fins 16 projecting from the housing, that act as a heat sink to conduct heat away from the lamp to the surrounding air, where it is carried away by convection. The housing is retained on the headband 18 by a pivot 20. A transverse member 22 fits over the crown of the user's head. Both the headband and the transverse member can be adjusted in length to fit the heads of different users. Power to the lamp and fan is supplied from a rechargeable battery 24. (Alternatively, power may supplied from a wall socket, or from any other suitable source of electricity.) The battery is shown as having been removed from a pouch 26 attached to a belt 28 by which it may be retained on the user's body. The length of the belt may be adjusted to fit the waists of different users. The pouch is opened and closed by a zipper 30, which is shown in an open position. Two wires 32 attached to poles 34 of the battery join to form a first insulated cord 36 that at its other end is connected to a moveable electrical socket 38. A second insulated cord 40 is electrically connected at its first end 42 to the lamp and fan and at its second end 44 to a plug 46. (The second cord passes under padding on the headband near its first end.) An indicator light 48 is on when electric current is flowing through the plug, and off when it is not. The power supply from the battery to the lamp and fan is shown as being disconnected, as the plug and socket are separated.

Figure 2:
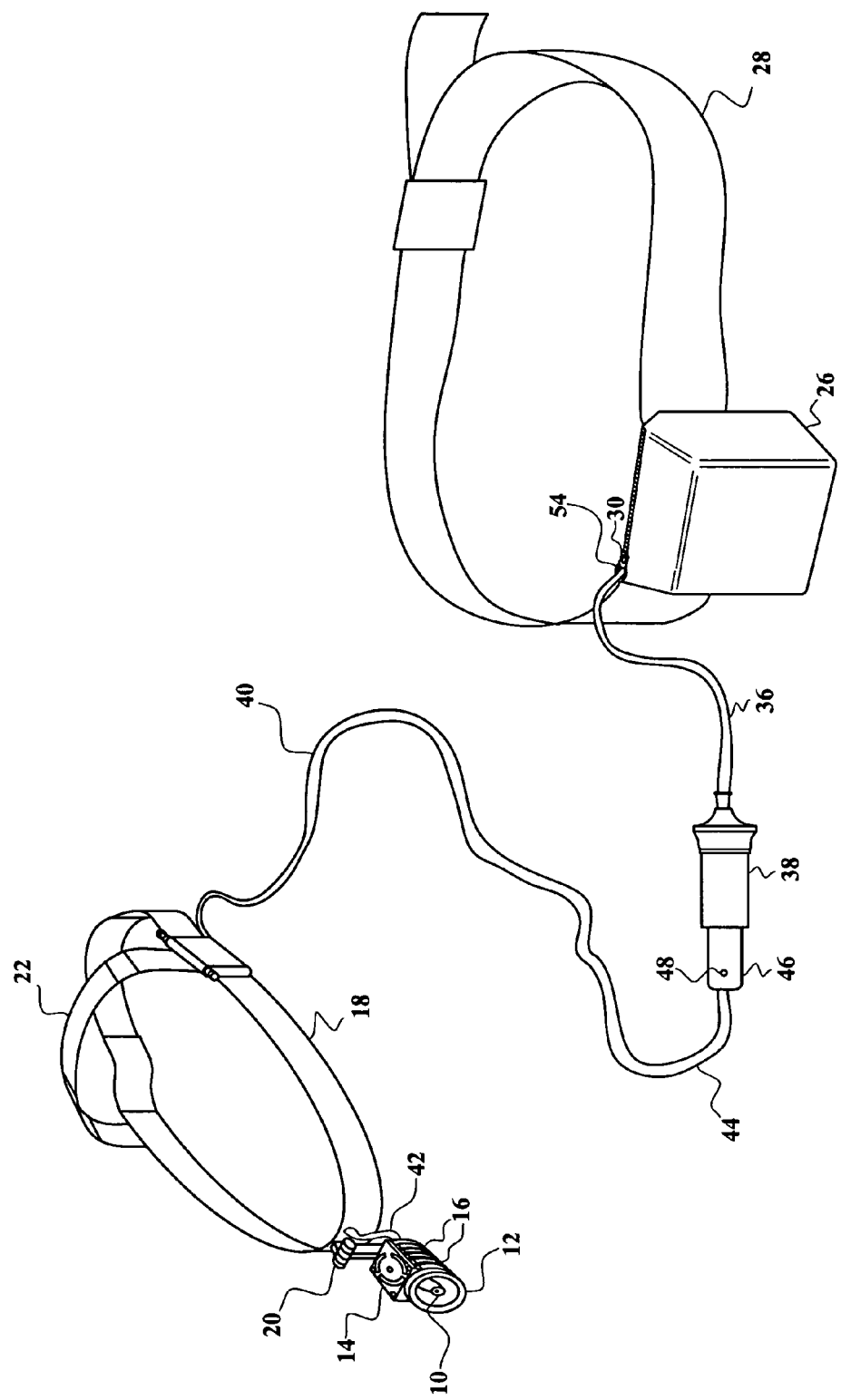
FIG. 2 is schematic perspective view of the preferred embodiment of the invention, with the power supply from the battery to the lamp and fan being connected, and the battery having been placed inside its pouch.

FIG. 2 is schematic perspective view of the preferred embodiment of the invention, with the power supply from the battery to the lamp and fan being connected by the insertion of the plug 46 into the socket 38. The lamp and fan will now be activated, provided that the switch 50 is in an on position. The switch has a cylindrical button 52, which is slid by the user in a straight line one way to turn it on, and in a straight line in the opposite direction to turn it off, without pivoting. (Alternatively, any other suitable kind of switch may be used.) The battery has been placed inside its pouch 26, which has been closed by the zipper 30, except for a small aperture 54 through which the first insulated cord 36 can pass.

Figure 3:
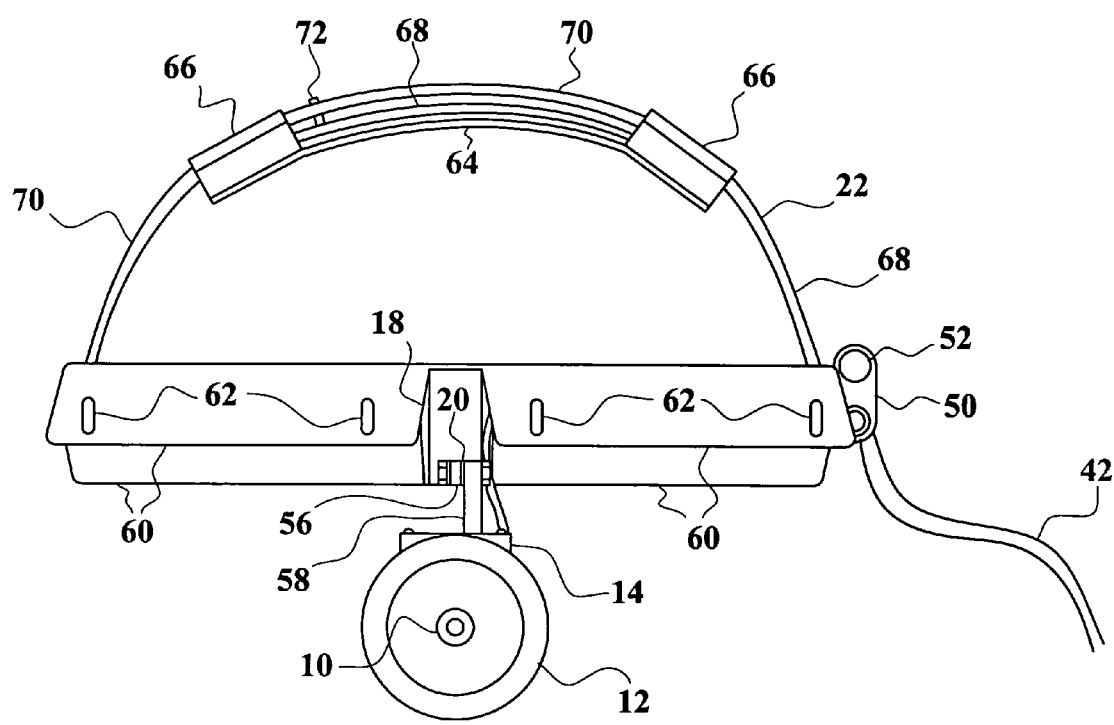
FIG. 3 is a front elevational view of the preferred embodiment of the invention.

FIG. 3 is a front elevational view of the preferred embodiment of the invention, showing first attachment member 56 extending from the headband 18, and second attachment member 58 extending from the lamp housing 12, joined at pivot 20. The front part of the headband is covered by front padding 60, which is folded over the headband and removably retained by retention bars 62. The bottom side of the transverse member 22 is covered by top padding 64, which is removably retained on the transverse member by strips of hook and loop fasteners 66. The transverse member comprises a left flap 68 and a right flap 70, which overlap in the middle and top of the transverse member. At the end of the right flap is buckle (covered by a stip of hook and loop fasteners in FIG. 3) through which the left flap slides to adjust the length of the transverse member. Extending upwards from the left flap is a prong 72, which passes through one of several holes (not visible in FIG. 3) in the right flap to retain the flaps in a fixed position. (It may be necessary to remove the top padding when adjusting the length of the transverse member.)

Figure 4:
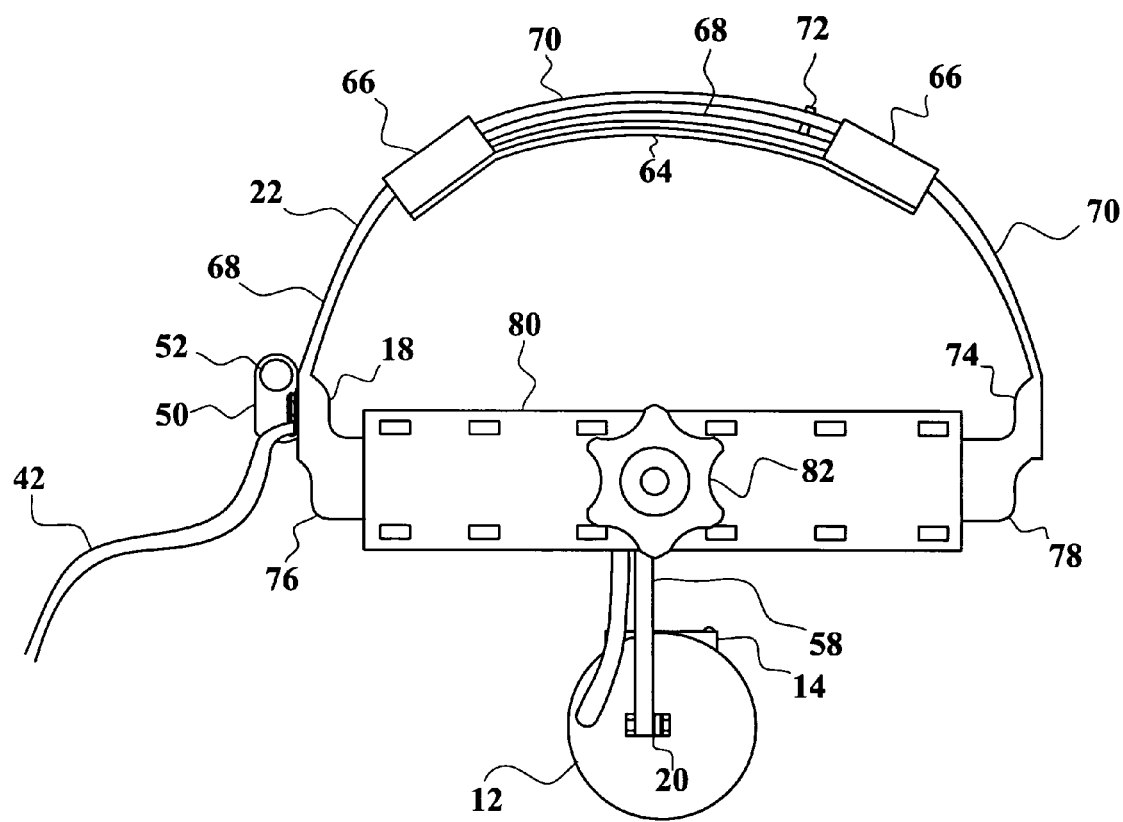
FIG. 4 is a rear elevational view of the preferred embodiment of the invention.

FIG. 4 is a rear elevational view of the preferred embodiment of the invention, showing the first part 74 of the headband 18, having a left side 76 and a right side 78, and the second part 80 of the headband, being an open-ended, flat, tubular casing, within which the ends of the left and right sides of the first part are inserted. A knob 82 on the second part can be turned clockwise to pull the opposite ends of the first part together, thereby reducing the circumference of the headband, or be turned counterclockwise to push the ends apart, thereby increasing the circumference of the headband, so that it can be adjusted for different users. (Alternatively, these directions can be reversed, so that the knob can be turned clockwise to pull the opposite ends of the first part together, thereby reducing the circumference of the headband, or be turned counterclockwise to push the ends apart, thereby increasing the circumference of the headband.)

Figure 5:
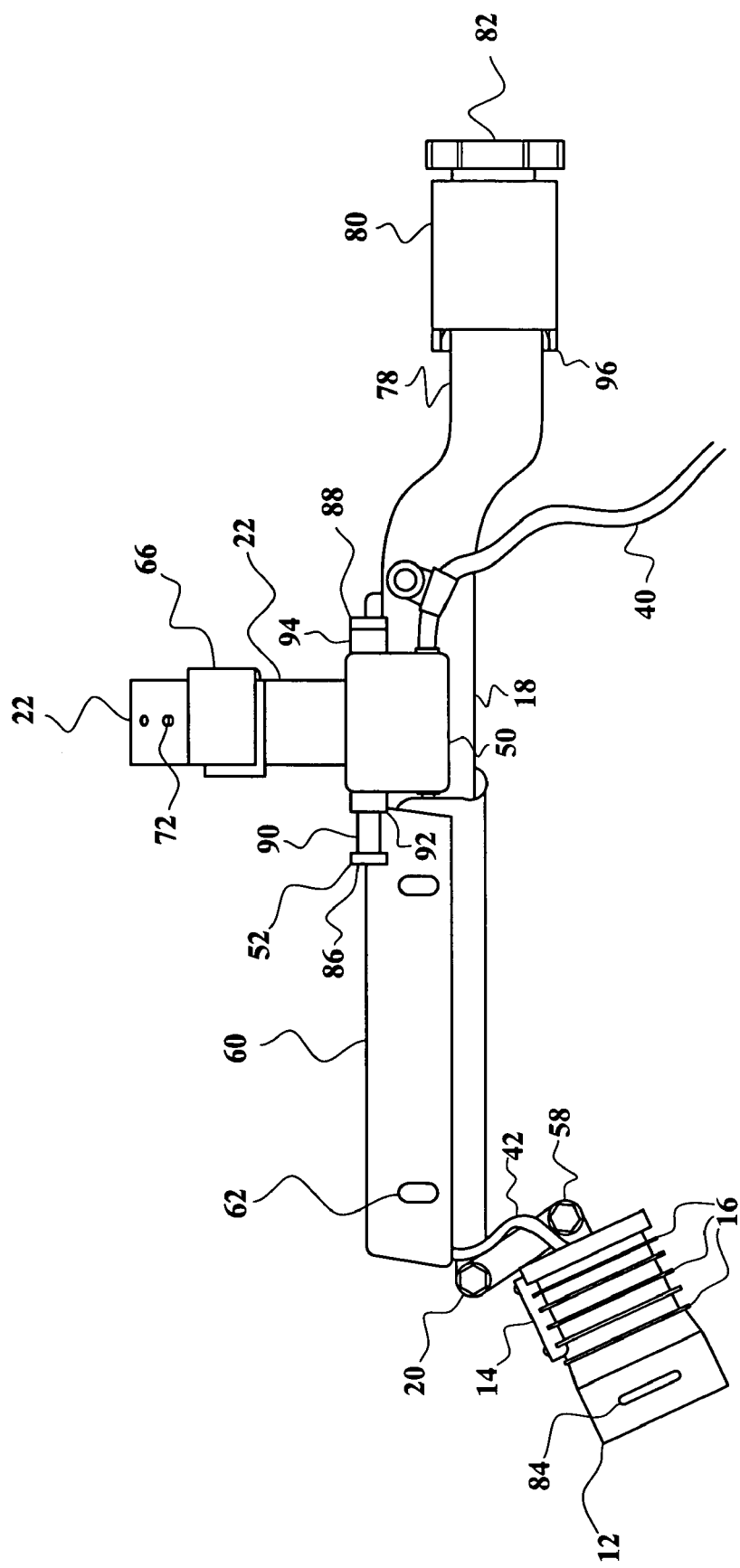
FIG. 5 is a left side elevational view of the preferred embodiment of the invention, with the lamp in a lowered position and the switch turned off.

FIG. 5 is a left side elevational view of the preferred embodiment of the invention, with the lamp and its housing 12 in a lowered position and the switch 50 turned off. An air vent 84 in the housing helps cool the lamp. The left slot 85 of the second part of the headband is shown, into which the end of the left side 76 of the first part of the headband is inserted. The cylindrical button 52 has a flat cylindrical first end 86, and an opposite flat cylindrical second end 88, between which is a cylindrical shaft 90, which has a smaller diameter than the ends, and fits within first socket 92 and second socket 94. It can be seen that when the cylindrical button 52 is in the off position, its first end 86 lies away from the first socket 92, while its second end 88 contacts the second socket 94.

Figure 6:
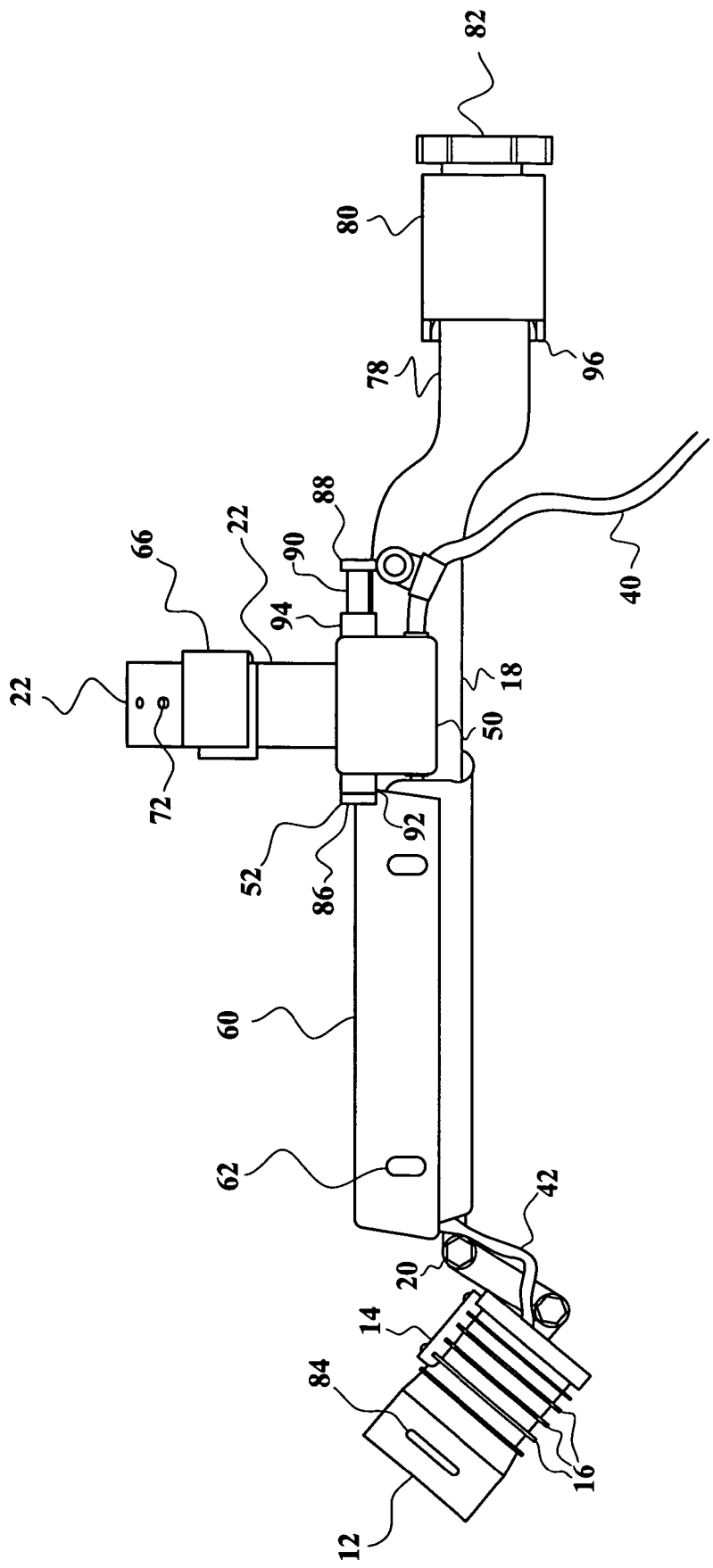

FIG. 6 is a left side elevational view of the preferred embodiment of the invention, with the lamp and its housing 12 in a raised position and the switch 50 turned on. It can be seen that when the cylindrical button 52 is in the on position, its first end 86 contacts the first socket 92, while its second end 88 lies away from the second socket 94.

Figure 7:
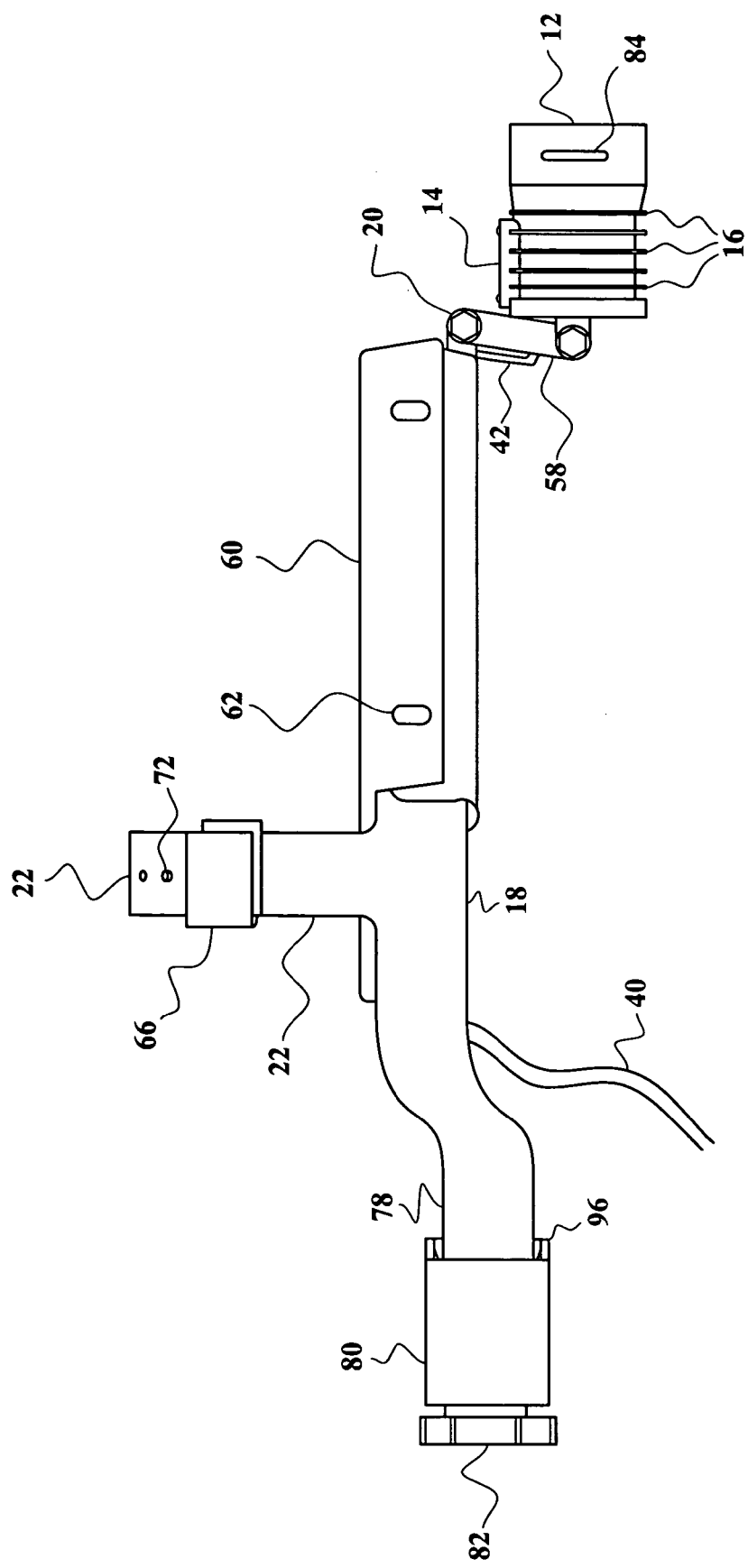
FIG. 7 is a right side elevational view of the preferred embodiment of the invention.

FIG. 7 is a right side elevational view of the preferred embodiment of the invention. The right slot 96 of the second part of the headband is shown, into which the end of the right side 78 of the first part of the headband is inserted. The lamp and its housing 12 are in an intermediate position, pointed straight ahead. The pivot 20 has a horizontal axis, and the lamp and its housing may be pointed at any angle along a vertical range of movement. The lamp may be moved horizontally or diagonally by moving the headband. (Alternatively, the pivot may be orientated so that the lamp can be moved horizontally or diagonally, or a ball and socket bearing may be substituted for the pivot to allow a range of motion in more than one dimension.)

Figure 8:
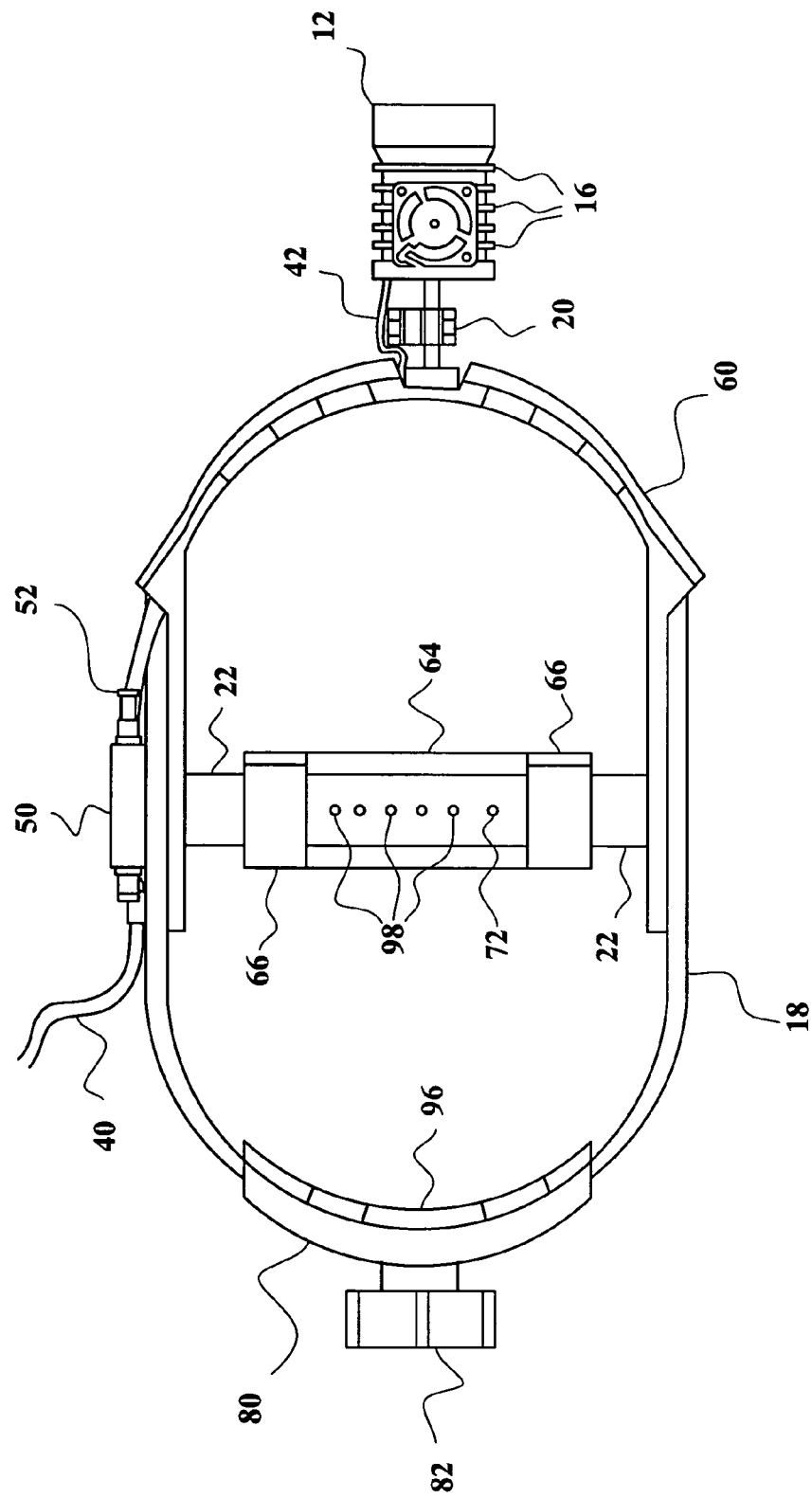
FIG. 8 is a top plan view of the preferred embodiment of the invention.
Figure 9:
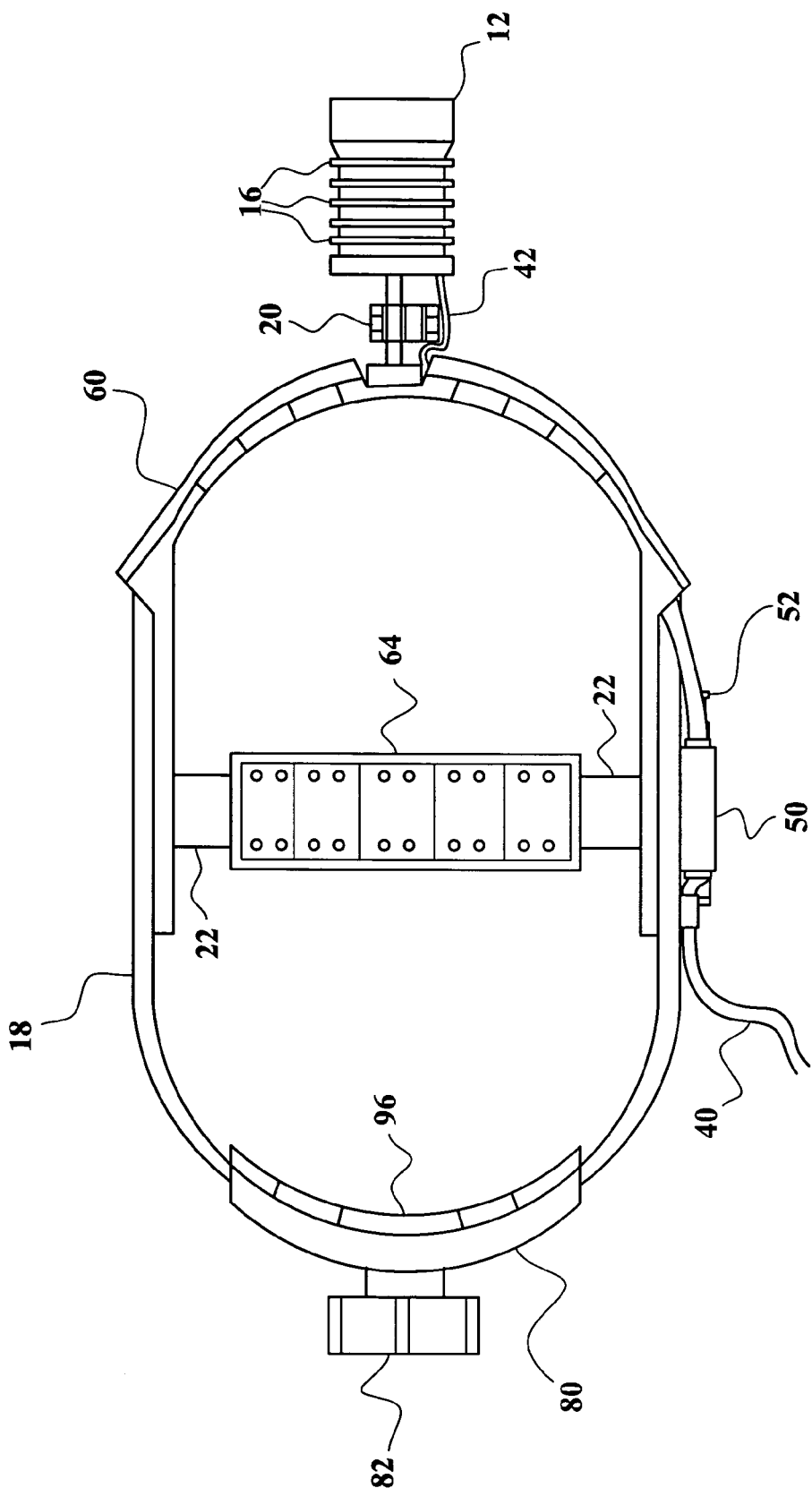
FIG. 9 is a bottom plan view of the preferred embodiment of the invention.

FIG. 8 is a top plan view of the preferred embodiment of the invention, showing rear padding 96 on the inside surface of the second part of the headband, strips of hook and loop fasteners 66 that retain the top padding 64 on the bottom of the transverse member 22, and the holes 98 in the transverse member through which the prong 72 can be inserted to adjust the length of the transverse member. FIG. 9 is a bottom plan view of the preferred embodiment of the invention, more clearly showing the top padding 64.

It is to be understood that the present invention is not limited to the sole embodiment described above, but encompasses any and all embodiments within the scope of the following claims.

We claim:

1. A light to be worn on a user's head, comprising:
    a light source;
    a housing for the light source;
    cooling fins that project from the housing;
    a fan that can cool the light source; and
    a headband on which the housing is retained; whereby the light source may be retained on a user's head.

2. The light to be worn on a user's head according to claim 1, wherein the light source is an electric lamp.

3. The light to be worn on a user's head according to claim 2, wherein the light source is a halogen lamp.

4. The light to be worn on a user's head according to claim 1, wherein the fan is mounted in a side wall of the housing.

5. The light to be worn on a user's head according to claim 1, wherein the housing is pivotally mounted on the headband.

6. The light to be worn on a user's head according to claim 5, wherein the housing can pivot vertically.

7. The light to be worn on a user's head according to claim 1, wherein the circumference of the headband can be adjusted, whereby the headband will fit heads of different users.

8. The light to be worn on a user's head according to claim 7, wherein:
    the headband has a first part with two opposite ends, and a second part with two opposite slots into each of which an end of the first part is inserted, and a knob on the second part;
    said knob can be turned in a first direction to pull the opposite ends of the first part together, thereby reducing the circumference of the headband; and
    said knob can be turned in an opposite second direction to push the ends apart, thereby increasing the circumference of the headband.

9. The light to be worn on a user's head according to claim 8, wherein the headband has a transverse strip with an adjustable length, whereby the headband can be more securely retained on heads of different users.

10. The light to be worn on a user's head according to claim 9, wherein at least one stip of padded material is retained on the headband.

11. The light to be worn on a user's head according to claim 10, wherein at least one of said strips of padded material is removably retained on the transverse strip by at least one strip of hook and loop fasteners.

12. The light to be worn on a user's head according to claim 1, wherein the light source and the fan are activated by a single source of electric power.

13. The light to be worn on a user's head according to claim 12, including a switch having a user moveable element that:
    when moved to a first position closes an electrical circuit between the single source of electrical power and the light source and the fan, thereby activating the light source and the fan; and
    when moved to second position opens the electrical circuit between the single source of electrical power and the light source and the fan, thereby deactivating the light source and the fan.

14. The light to be worn on a user's head according to claim 13, wherein the user moveable element moves in a first linear direction when moved from the second position to the first position, and in an opposite second linear direction when moved from the first position to the second position, without pivoting.

15. The light to be worn on a user's head according to claim 14, wherein the user moveable element has a first end that contacts a first socket in the first position and lies away from the first socket in the second position, and an opposite second end that lies away from a second socket in the first position and contacts the second socket in the second position.

16. The light to be worn on a user's head according to claim 15, wherein:
    the first end and the second end of the user moveable element are flat cylinders;
    the user moveable element has a cylindrical shaft between its first end and its second end; and
    the cylindrical shaft has a smaller diameter than said ends.

17. The light to be worn on a user's head according to claim 16, wherein the single power source is a rechargeable battery.

18. The light to be worn on a user's head according to claim 17, including:
    wires connected to poles of the rechargeable battery that join to form a first cord that is connected to a moveable electrical socket; and
    a second cord, having a first end that is electrically connected to the light source and the fan, and a second end that is connected to a plug;
    wherein, if the plug is inserted into the moveable electrical socket, and the user moveable element of the switch is in the first position, electrical power from the rechargeable battery can activate the light source and the fan.

19. The light to be worn on a user's head according to claim 18, including:
    a pouch within which the rechargeable battery can be retained;
    a zipper, which when moved in a first direction opens the pouch to permit insertion of the rechargeable battery, and when moved in a second direction closes the pouch, except for a small aperture through which the first cord can pass, to more securely retain the rechargeable batter.

20. The light to be worn on a user's head according to claim 19, wherein the pouch is retained on an adjustable belt, by which the pouch can be retained on a user's body.

* * * * *